(12) United States Patent
Kato

(10) Patent No.: US 7,374,543 B2
(45) Date of Patent: May 20, 2008

(54) WRIST SPHYGMOMANOMETER AND CUFF SPRING FOR THE SAME

(75) Inventor: Junichi Kato, Gunma (JP)

(73) Assignee: Nihon Seimitsu Sokki Co., Ltd., Gunma (JP)

( * ) Notice: Subject to any disclaimer, the term of this patent is extended or adjusted under 35 U.S.C. 154(b) by 101 days.

(21) Appl. No.: 10/970,723

(22) Filed: Oct. 22, 2004

(65) Prior Publication Data

US 2005/0283084 A1 Dec. 22, 2005

(30) Foreign Application Priority Data

Oct. 24, 2003 (JP) ............................. 2003-364466

(51) Int. Cl.
*A61B 5/00* (2006.01)
(52) U.S. Cl. ....................... 600/499; 600/490
(58) Field of Classification Search ................. 600/499
See application file for complete search history.

(56) References Cited

U.S. PATENT DOCUMENTS 3,633,567 A * 1/1972 Sarnoff ........................ 600/499
4,549,550 A * 10/1985 Kami .......................... 600/499
5,840,037 A * 11/1998 Tochikubo et al. .......... 600/499
6,338,723 B1 * 1/2002 Carpenter et al. ............ 602/75
2003/0088267 A1  5/2003 Itonaga et al.
2004/0193084 A1 * 9/2004 Ravikumar ................... 602/13

FOREIGN PATENT DOCUMENTS

EP          0 392 702 A1   10/1990
EP          1 256 313 A2   11/2002

OTHER PUBLICATIONS

Patent Abstracts of Japan, vol. 2000, No. 02, Feb. 29, 2000.
Patent Abstracts of Japan, vol. 0150, No. 76 (C-0809), Feb. 21, 1991.

* cited by examiner

*Primary Examiner*—Robert L Nasser
(74) *Attorney, Agent, or Firm*—Venable LLP; Catherine M. Voorhees

(57) ABSTRACT

To improve measurement accuracy of blood pressure. A wrist sphygmomanometer comprises a cuff spring formed in a curved shape to fit the semicircle on the side of the pulsation part of the wrist, having a mount portion formed outside; a cuff band including the cuff spring as a core material, having an air bag inside, and wound around a wrist; and a sphygmomanometer main body mounted on the mount portion of the cuff spring, having a pressure pump for supplying air to the air bag, wherein the cuff spring has a protrusion protruding inward formed in a nearly central position in a peripheral direction.

3 Claims, 5 Drawing Sheets

WRIST SPHYGMOMANOMETER AND CUFF SPRING FOR THE SAME

FIELD OF THE INVENTION

The present invention relates to a wrist sphygmomanometer, which is mounted on a wrist and is capable of measuring blood pressure, and a cuff spring used as a core material of the cuff band of the wrist sphygmomanometer.

DESCRIPTION OF THE RELATED ART

Generally, a conventional sphygmomanometer that functions to measure blood pressure by placing a cuff band on an upper arm has been mainly used. However, as a sphygmomanometer to measure blood pressure by an oscillometric method is becoming available for practical use, a sphygmomanometer which makes it possible to measure blood pressure by the wrist as described in Patent Document 1, is proposed.

As shown in FIG. 5, the sphygmomanometer 50 is an integral type manometer in which a cuff band 52 wound around a wrist 100 is unified to a sphygmomanometer main body 51. An air bag 54 is disposed inside the cuff band 52, and air is supplied to the air bag 54 from the sphygmomanometer main body 51 to expand the air bag, which presses against arteries (ulnar artery 101, and radial artery 102) passing along the wrist 100 to measure blood pressure. Incidentally, numerals 104, 105, and 106 in FIG. 5 indicate a tendon, the ulna, and a radius, respectively.

(Patent Document 1)
Japanese Patent Application Laid-open No. Hei 11-299748

However, the cuff spring (clip plate) 53 included in the cuff band 52 as a core material of the cuff band 52 is formed in a curved surface to fit the semicircle on the side of the pulsation part of the wrist 100 where the ulnar artery 101, the radial artery 102, and the tendon 104 are positioned. Therefore, when the cuff band 52 is wound around the wrist 100, and air is supplied from the sphygmomanometer main body 51 to the air bag 54 to expand the air bag 54 with the cuff spring 53 properly fit the semicircle on the side of the pulsation part 103 of the wrist 100, in some cases, the expanded portion of the air bag 54 is not properly formed near the ulnar artery 101 and the radial artery 102, and cannot suitably press these ulnar artery 101 and radial artery 102. In such a case, there is a possibility that the blood pressure cannot be measured with high accuracy.

Other conventional sphygmomanometers includes the one in which the air bag of the cuff band is divided into two portions at the center in a peripheral direction of the cuff spring, and air is supplied to the respective air bags so that the expanded portions of the respective air bags press the ulnar artery 101 and the radial artery 102 individually. However, in this case, since the air bag is separated, a problem is that the cuff band is difficult to be wound around the wrist 100.

Further, in the conventional sphygmomanometer 50 in FIG. 5, the cuff spring 53 inside the cuff band 52 is substantially an elliptical cylinder having an arc shaped cross section of which a portion is cut out in a peripheral direction. The curvature of the cuff spring 53 is constant in an axial direction of the cuff spring 53. On the other hand, since the wrist 100 around which the cuff band 52 is wound gradually enlarges from the hand towards the arm, when the cuff band 52 bundling the cuff spring 53 is wound around the wrist 100, the cuff spring 53 does not fit the wrist 100, and the cuff band 52 is apt to shift in the longitudinal and peripheral directions of the wrist 100. Accordingly, measurement of blood pressure with the sphygmomanometer 50 is not stable in this case, and the accuracy of blood pressure measurement is lowered.

SUMMARY OF THE INVENTION

In view of the above-described circumstances, the present invention is provided, and an object of the present invention is to provide a wrist sphygmomanometer capable of accurately measuring blood pressure, and a cuff spring used as a core material of a cuff band for the wrist sphygmomanometer.

A first aspect of the present invention provides a wrist sphygmomanometer formed in a curved shape to fit the semicircle on the side of the pulsation part of the wrist, comprising:

a cuff spring having a mount portion outside;

a cuff band including the cuff spring as a core, having an air bag disposed inside, and wound around the wrist; and a sphygmomanometer main body mounted on the mount portion of the cuff spring, comprising a pressure pump for supplying air to the air bag, wherein the cuff spring has a protrusion protruding inward formed at a nearly central position in a peripheral direction.

A second aspect of the present invention provides a wrist sphygmomanometer formed in a curved shape to fit the semicircle on the side of the pulsation part of the wrist, comprising:

a cuff spring having a mount portion outside;

a cuff band including the cuff spring as a core, having an air bag disposed inside, and wound around the wrist; and a sphygmomanometer main body mounted on the mount portion of the cuff spring, comprising a pressure pump for supplying air to the air bag, wherein the cuff spring has a slit formed at an arbitrary position in the axial direction so as to extend in the peripheral direction, and both sides of the slit in the axial direction of the cuff spring are formed having different curvatures with each other.

A third aspect of the present invention provides a wrist sphygmomanometer formed in a curved shape to fit the semicircle on the side of the pulsation part of the wrist, comprising:

a cuff spring having a mount portion outside;

a cuff band including the cuff spring as a core, having an air bag disposed inside, and wound around the wrist; and a sphygmomanometer main body mounted on the mount portion of the cuff spring, comprising a pressure pump for supplying air to the air bag, wherein the cuff spring has a protrusion protruding inward formed at a nearly central position in the peripheral direction, the cuff spring has a slit formed at an arbitrary position in the axial direction so as to extend in a peripheral direction, and both sides of the slit in the axial direction of the cuff spring are formed having different curvatures with each other.

A fourth aspect of the present invention provides the wrist sphygmomanometer according to either of aspects 1 or 3 of the present invention, the cuff spring is provided with an reinforcing rib formed integrally with the protrusion to reinforce the protrusion.

A fifth aspect of the present invention provides a cuff spring used as a core material of a cuff band of a wrist sphygmomanometer, wherein a plate-like elastic member is formed in a curved shape to fit the semicircle on the side of the pulsation part of the wrist, and a protrusion protruding inward is provided at a nearly central position in the peripheral direction.

A sixth aspect of the present invention provides a cuff spring used as a core material of a cuff band of a wrist sphygmomanometer, wherein a plate-like elastic member is formed in a curved shape to fit the semicircle on the side of the pulsation part of the wrist, a slit extending in a peripheral direction is formed in an arbitrary position of the axial direction, and both sides of the slit in the axial direction of the cuff spring are formed having different curvatures with each other.

A seventh aspect of the present invention provides a wrist sphygmomanometer, comprising:

a cuff band including the cuff spring of aspects 5 or 6 of the present invention as a core material, having an air bag disposed inside, and wound around the wrist; and a pressure pump provided separately from the cuff band for supplying air to the air bag of the cuff band.

According to the aspects 1 or 3, a sphygmomanometer main body having a pressure pump is mounted on a mount portion, and a cuff spring having a curved shape becoming a core material of a cuff band to be wound around a wrist has a protrusion protruding inward formed in a nearly central position in the peripheral direction. Thus, the protrusion is positioned between positions corresponding to each of the two arteries passing through the pulsation part of the wrist in the peripheral direction of the cuff spring, when the cuff band is wound around the wrist with the cuff spring properly fit the semicircle on the side of the pulsation part of the wrist. Therefore, when air is supplied from the pressure pump of the sphygmomanometer main body to the air bag of the cuff band, the air bag avoids the protrusion in the peripheral direction of the cuff spring and adequately expands at both sides of the protrusion. Therefore, each of the two arteries of the wrist can be effectively pressed by the expanded portions, thereby improving measurement accuracy of the blood pressure.

According to the aspects 2 or 3 of the present invention, the cuff spring has a slit extending in the peripheral direction formed at an arbitrary position in the axial direction, and both sides of the slit in the axial direction of the cuff spring are formed having different curvatures with each other, which contributes to fitting the semicircle on the side of the pulsation part of the wrist of which a thickness changes gradually, so that the space between the cuff band and the wrist can be reduced when the cuff band is wound around the wrist. As a result, since the cuff band can be prevented from shifting in the longitudinal direction and in the peripheral direction of the wrist, blood pressure can be stably measured so that the accuracy in blood pressure measurement can be improved.

According to the aspect 4 of the present invention, since the reinforcing rib to reinforce the protrusion is provided integrally with the protrusion on the cuff spring, the rigidity of the protrusion is increased. As a result, deformation of the protrusion can be prevented, and the expanded portions of the air bag formed on both sides of the protrusion in the peripheral direction of the cuff spring can press more effectively the arteries passing along the wrist.

According to the aspects 5 to 6 of the present invention, the cuff spring used for the wrist sphygmomanometer according to aspects 1 or 3 can be obtained. Besides, according to the invention described in aspect 7, the wrist sphygmomanometer in which the cuff band and the sphygmomanometer main body are provided separately can be obtained.

BRIEF DESCRIPTION OF THE DRAWINGS

FIG. 3A and FIG. 3B show a cuff spring in FIG. 2, wherein FIG. 3A is a plan view and FIG. 3B is a side view;

DETAILED DESCRIPTION OF THE PREFERRED EMBODIMENT(S)

Hereinafter, preferred embodiments to carry out the present invention will be explained based on the drawings.

Figure 1:
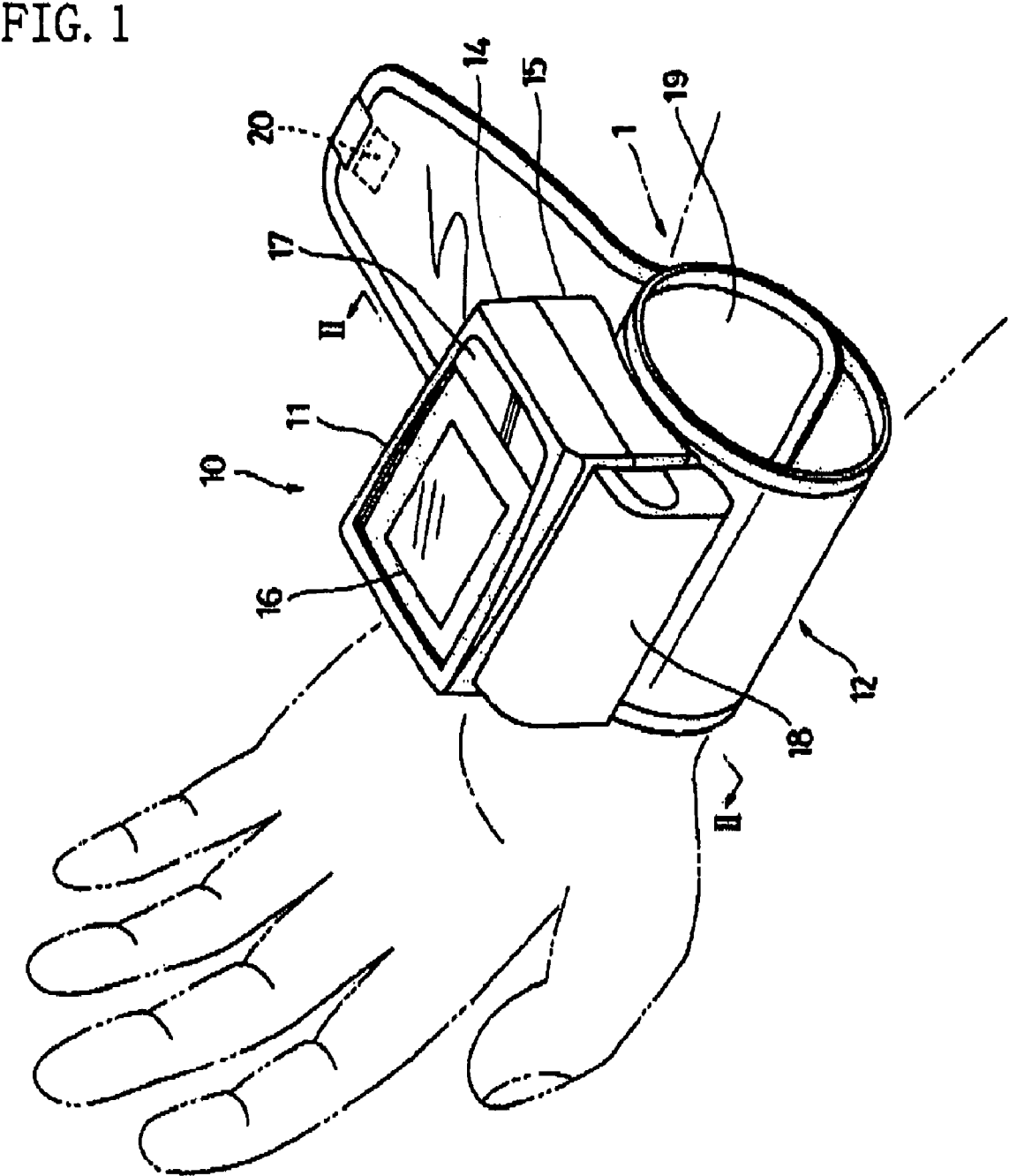
FIG. 1 is a perspective view showing an embodiment of a wrist sphygmomanometer relating to the present invention.
Figure 2:
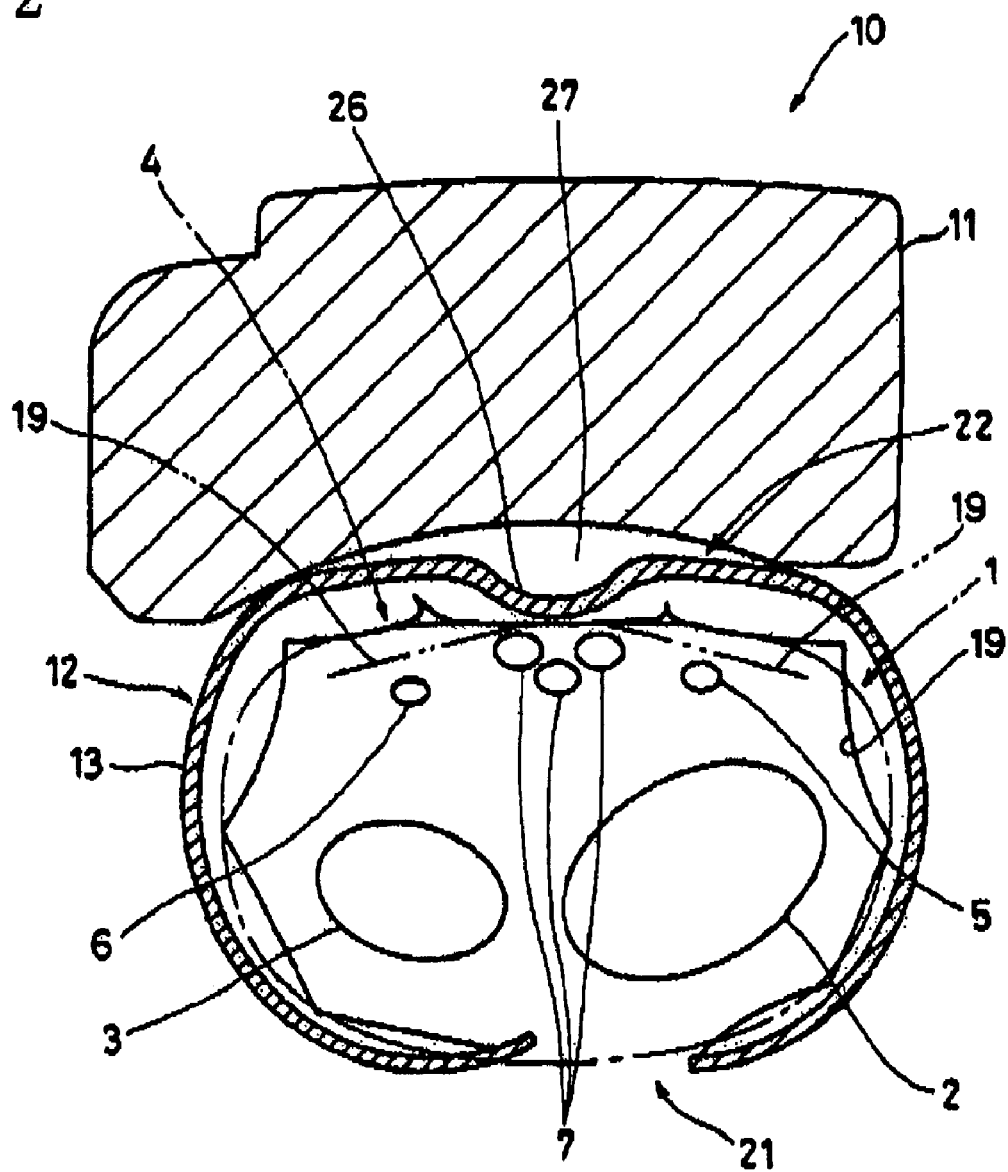
FIG. 2 is a sectional view taken along the II-II line in FIG. 1.

FIG. 1 is a perspective view showing an embodiment of a wrist sphygmomanometer relating to the present invention. FIG. 2 is a sectional view taken along the II-II line in FIG. 1.

The wrist sphygmomanometer 10 shown in FIG. 1 includes a sphygmomanometer main body 11 and a cuff band 12 attached to the sphygmomanometer main body, in which the sphygmomanometer main body 11 is mounted on a wrist 1 by winding the cuff band 12 around the wrist 1 to carry out measurement of blood pressure using an oscillometric method. The wrist sphygmomanometer 10 comprises the sphygmomanometer main body 11, the cuff band 12, and a cuff spring 13.

In the inside of the wrist 1, as shown in FIG. 2, in addition to an ulna 2 and a radius 3 passing in parallel, an ulnar artery 5 and a radial artery 6 also pass in parallel. These ulnar artery 5 and radial artery 6 are placed on one side of the ulna 2 and the radius 3 in the wrist 1, namely, placed at an interval in the radial pulse region 4 of the wrist 1. Furthermore, in a radial pulse region 4 of the wrist 1, a plurality of tendons 7 pass positioned between the ulnar artery 5 and the radial artery 6.

In the sphygmomanometer main body 11, main machineries for measuring blood pressure such as a pressure pump, a control valve for reduction of pressure, a pressure sensor, and a controller to control these equipment (not shown) are housed in an upper case 14 and a lower case 15 which are joined at their opening sides to each other as shown in FIG. 1. And a liquid crystal display portion 16 and various switches 17 are disposed on the top face of the upper case 14. Further, on a side of the sphygmomanometer main body 11, a battery 18 is installed. On the display portion 16, measured blood pressure or pulse count is displayed, for instance, with digital display.

The cuff band 12 includes the cuff spring 13 having a curved surface as a core material, as will be described in detail later, and has an air bag 19 disposed inside as shown in FIG. 1 and FIG. 2. The cuff band 12 is wound around the wrist 1 and fixed using a face fastener 20 provided inside. Air is supplied from the pressure pump of the sphygmomanometer main body 11 to the air bag 19 of the cuff band 12 in a state that the cuff band 12 is wound and fixed around the wrist 1, so that the wrist 1 is pressed by the air pressure.

The cuff spring 13 is formed with flexible synthetic resin and the like, and molded in a curved surface to fit the semicircle on the side of the pulsation part 4 of the wrist 1 as shown in FIGS. 2, 3A, 3B, and 4. In short, the cuff spring 13 is substantially an elliptical cylinder having an elliptical arcuate shape cross section having a cut portion 21 from which a part in the peripheral direction is cut away wherein by enlarging the cut portion 21, the diameter is accordingly expanded, and by narrowing the cut portion 21, the diameter is accordingly reduced.

On the outer peripheral side of the cuff spring 13, a mount portion 22 is formed at a nearly central position in the peripheral direction so as to oppose to the removed portion 21. The mount portion 22 comprises a plurality of lock claw pieces 23 and a screwing piece 24, and these lock claw pieces 23 and screwing piece 24 are cut up from the cuff spring 13 so as to be formed integrally with the cuff spring 13. The lock claw pieces 23 are locked with the lower case 15 of the sphygmomanometer main body 11, and the screwing piece 24 is screwed thereto. Thus, the sphygmomanometer main body 11 is mounted on the mount portion 22 of the cuff spring 13. An opening 25 is formed on the mount portion 22. A communicating tube (not shown) communicating between the pressure pump of the sphygmomanometer main body 11 and the air bag 19 of the cuff band 12 is inserted through the opening 25.

An protrusion 26 protruding inward, for instance, in an arc shape, is formed on the cuff spring 13 at a nearly central position in the peripheral direction opposing to the cut portion 21 along the whole length of the cuff spring 13 in the axial direction. The protrusion 26 is placed at a position opposing to the tendon 7 in the pulsation part 4 of the wrist 1 so that the cuff spring 13 appropriately fits the semicircle on the side of the pulsation part 4 of the wrist 1, and when the cuff band 12 is wound around the wrist 1 in this state, the protrusion 26 is placed, as shown in FIG. 2, at a nearly central position between the positions respectively corresponding to the ulnar artery 5 and the radial artery 6 in the pulsation part 4 of the wrist 1 in the peripheral direction of the cuff spring 13. Through this formation, when air is supplied to the air bag 19 of the cuff band 12, the air bag 19 avoids the protrusion 26 in the peripheral direction of the cuffs spring 13, adequately expands as shown by the two-dot chain line in FIG. 2, at both sides of the protrusion bordered by the protrusion 26, and effectively presses ulnar artery 5 and the radial artery 6 on both sides of the tendon 7 in the wrist 1.

Figure 3A:
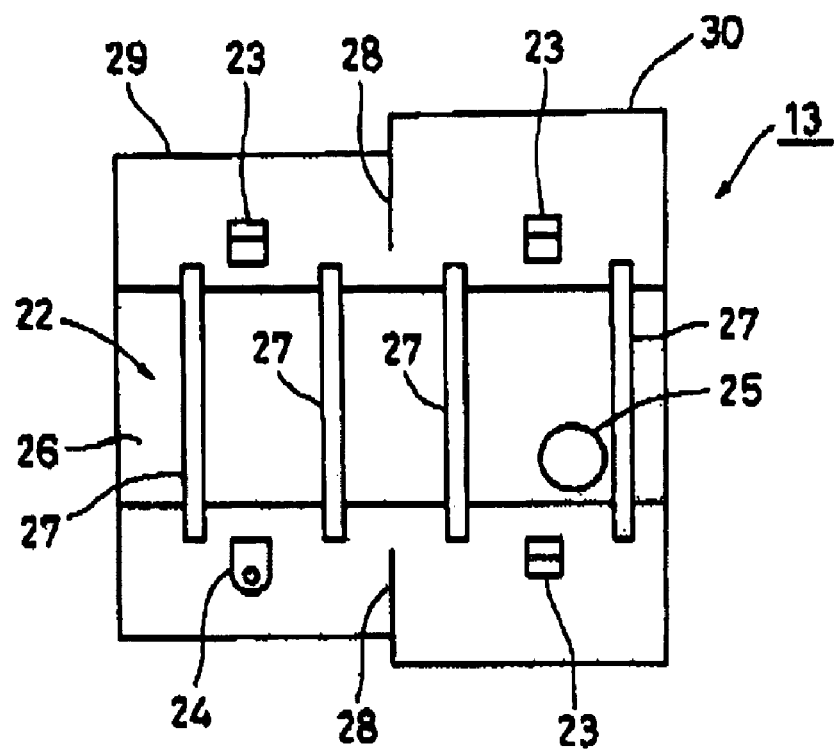
Figure 3B:
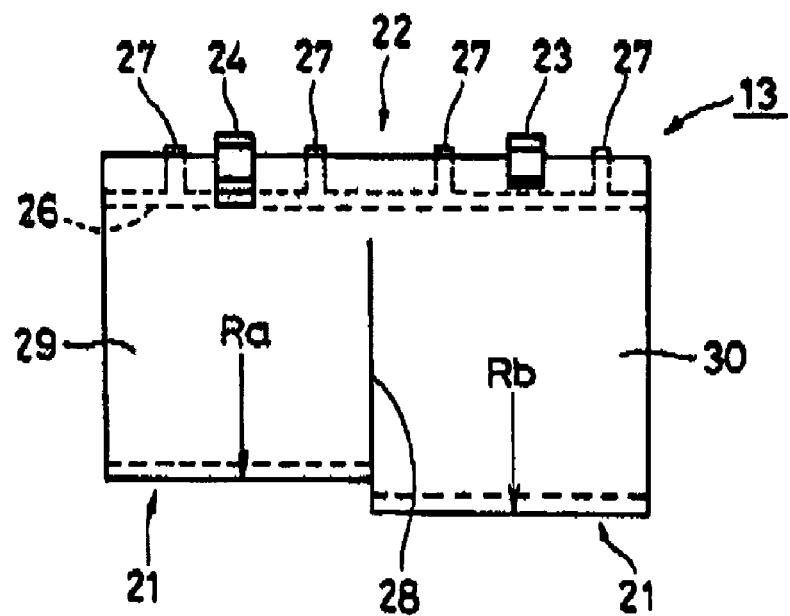

Within a region of the mount 22 in the outside periphery of the cuff spring 13, reinforcing ribs 27 are integrally formed with the protrusion 26 on the outside of the protrusion 26. A plurality of reinforcing ribs 27 are provided at predetermined intervals in the axial direction of the cuff spring 13 to reinforce the protrusion 26 so that rigidity of the protrusion 26 can be increased as shown in FIGS. 3A and 3B, and FIG. 4.

Figure 4:
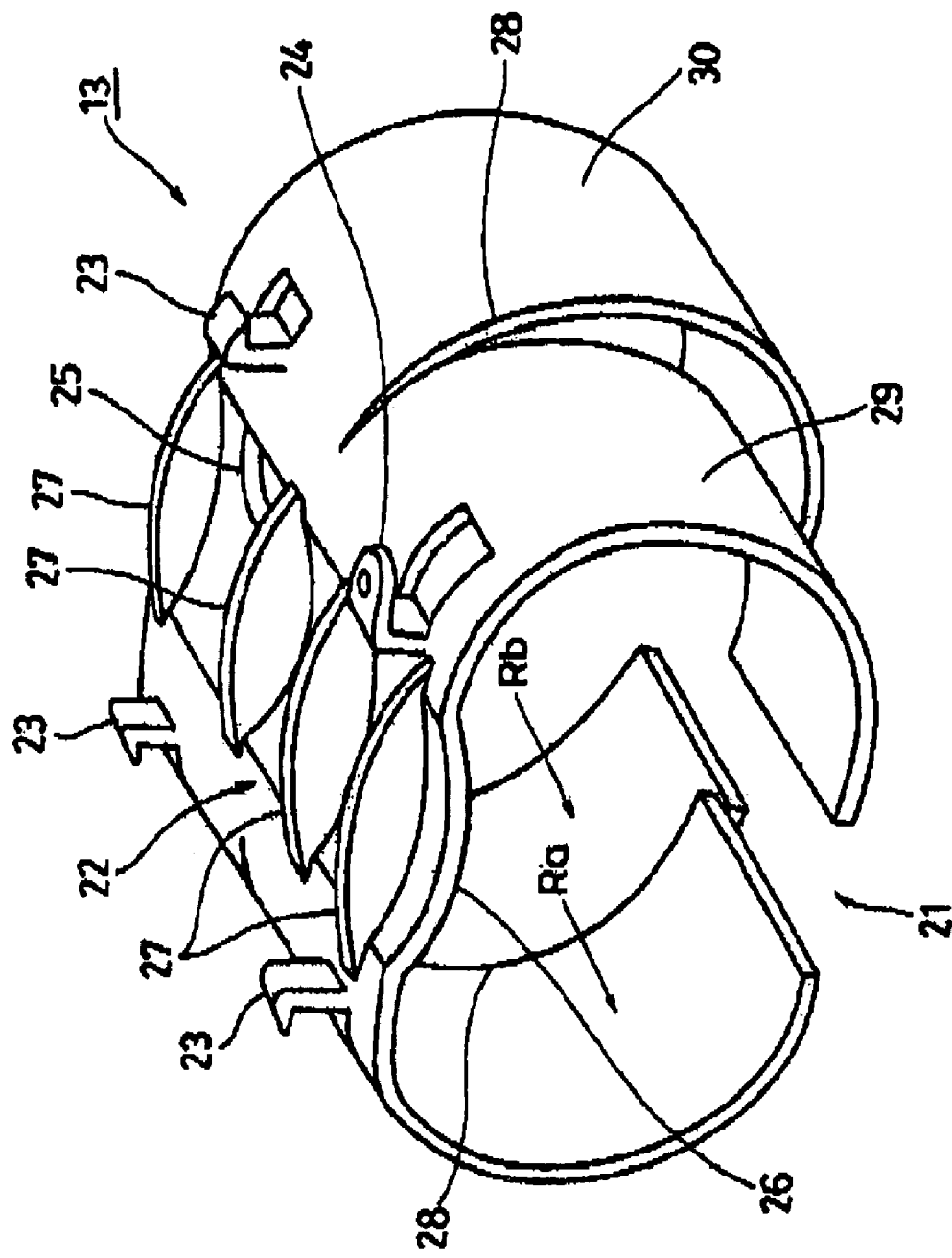
FIG. 4 is a perspective view of the cuff spring shown in FIG. 2.
Figure 5:
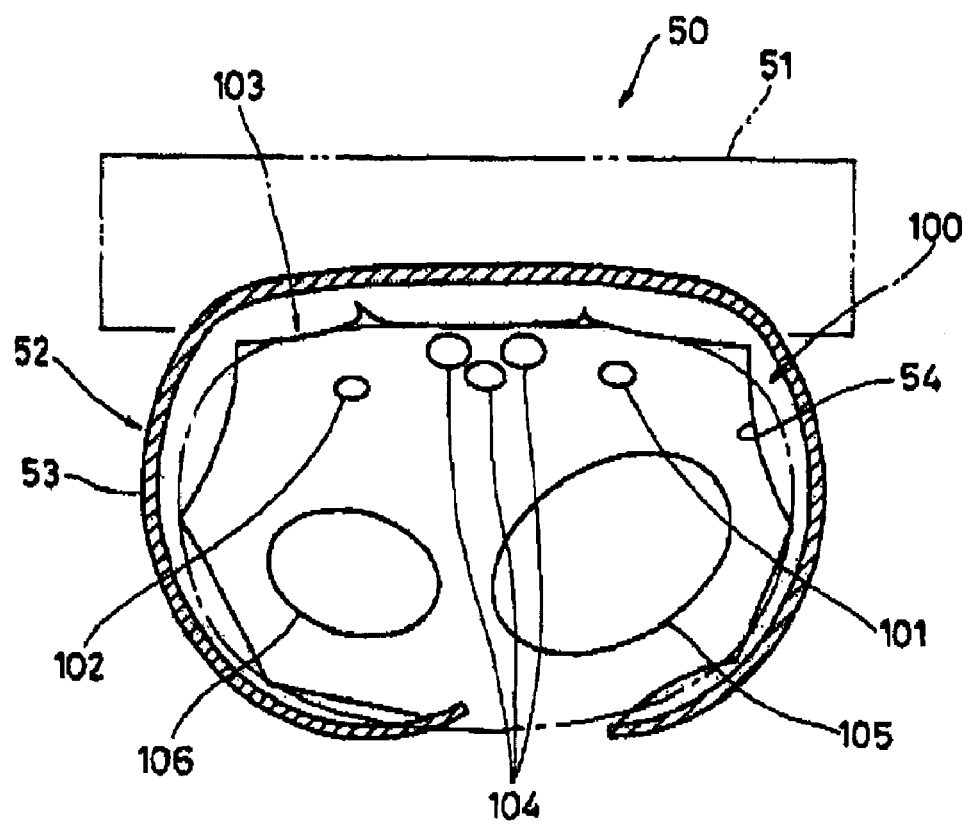
FIG. 5 is a sectional view showing a conventional wrist sphygmomanometer.

Besides, in the substantially elliptical shaped cuff spring 13, the slit 28 extending in the peripheral direction from the cut portion 21 to the mount portion 22 is formed, symmetrically in FIG. 4, at an optional position in the axial direction, in the present embodiment at the center position, in the axial direction. A portion excepting the mount portion 22 and the protrusion 26 of the cuff spring 13 is divided into a hand-side divided portion 29 and an arm-side divided portion 30 in the axial direction by these slits 28, and these two divided portions are formed having different curvatures. In short, curvature Rb of the arm-side divided portion 30 is formed larger than curvature Ra of the hand-side divided portion 29. Thereby, when the cuff band 12 is wound around the wrist 1, even though the wrist 1 gets thicker gradually from the hand side to the arm side, the cuff spring 13 of the cuff band 12 follows the changes in thickness of the wrist 1, to fit the semicircle on the side of the pulsation part 4 of the wrist 1. Namely, the space between the cuff band 12 and the wrist 1 is decreased.

The operation will be explained next.

The cuff band 12 is wound around the wrist 1 and fixed using the face fastener 20. At this time, the protrusion 26 on the cuff spring 13 in the cuff band 12 is placed so as to oppose to the tendon 7 on the side of the pulsation part 4 of the wrist 1 so that the cuff spring 13 adequately fit the semicircle on the side of the pulsation part 4 on the wrist 1. Then, the switches 17 of the sphygmomanometer main body 11 are turned on while the hand is lightly opened with the palm of a hand facing upward, with an elbow in touch with the top face of a desk or the like to keep the wrist 1 at the height of a heart.

Then, air is supplied from the pressure pump of the sphygmomanometer main body 11 to the air bag 19 of the cuff band 12 to expand the air bag 19. The air bag 19 adequately expands at both sides of the protrusion 26 in the peripheral direction of the cuff spring 13 in the cuff band 12 so that these expanded portions press effectively the ulnar artery 5 and the radial artery 6 which are on both sides of the tendons 7 in the wrist 1. During predetermined elapsed time in this state, blood pressure is measured by a pressure sensor or the like of the sphygmomanometer main body 11, and the measurement result is displayed on the display 16 of the sphygmomanometer main body 11.

With the above-described structure, the following effects (1) to (4) can be exhibited from the above embodiment.

(1) In the cuff spring 13 having a curved surface becoming a core material of the cuff band 12 which is wound around the wrist 1, the protrusion 26 protruding inward is formed at a nearly central position in the peripheral direction, and therefore when the protrusion 26 is positioned at a nearly central position between positions corresponding to each of the ulnar artery 5 and the radial artery 6 passing through the pulsation part 4 of the wrist 1 in the peripheral direction of the cuff spring 13, when the protrusion 26 is opposed to the tendons 7 on the side of the pulsation part 4 of the wrist 1 to adequately fit the semicircle on the side of the pulsation part 4 of the wrist 1 and in this state the cuff band 12 is wound around the wrist 1. Accordingly, when air is supplied from the pressure pump of the sphygmomanometer main body 11 to the air bag 19 of the cuff band 12, the air bag 19 avoids the protrusion 26 in the peripheral direction of the cuff spring 13, and adequately expands at both sides of the protrusion 26. Therefore, each of the ulnar artery 5 and the radial artery 6 positioned on both sides of the tendons 7 in the wrist 1 can be effectively pressed with the expanded portions, thereby improving the measurement accuracy of the blood pressure.

(2) In the cuff spring 13 in the cuff band 12, the protrusion 26 protruding inward is formed at a nearly central position in the peripheral direction. Thus, the protrusion 26 is opposed to the tendons 7 in the pulsation part 4 of the wrist 1 to fit the semicircle on the side of the pulsation part 4 of the wrist 1, and a feel of touch of the protrusion 26 is thereby given to a specific part in which the tendons 7 of the wrist 1 exist. Thus, when the cuff band 12 is wound around the wrist 1, it is possible to confirm that the protrusion 26 of the cuff spring 13 is adequately positioned on the side of the pulsation part 4 of the wrist 1, opposing to the tendons 7 of the wrist 1. Accordingly, pressing on the ulnar artery 5 and the radial artery 6 of the wrist 1 due to expansion of the air bag 19 of the cuff band 12 can be optimized, measurement of blood pressure is stabilized, and the blood pressure can be measured with accuracy.

(3) In the cuff spring 13, the reinforcing rib 27 reinforcing the protrusion 26 is integrally provided with the protrusion 26, and therefore the rigidity of the protrusion 26 is increased. Thus, deformation of the protrusion 26 can be prevented and also the pressure of the expanded portions of the air bag 19, which is formed on both sides of the protrusion 26 in the peripheral direction of the cuff spring 13, acts more effectively on the ulnar artery 5 and the radial artery 6 of the wrist 1.

(4) In the cuff spring 13, the slit 28 extending in the peripheral direction from the cut portion 21 to the mount portion 22 is formed in symmetry at a nearly central position in the axial direction, and curvature of the arm-side divided portion 30 is formed larger than the curvature of the hand-side divided portion 29 on both sides of the slit 28 in the axial direction of the cuff spring 13. Therefore, the cuff spring 13 can fit the surrounding of the wrist 1 gradually increasing in thickness from the hand side to the arm side. As a result, when the cuff band 12 is wound around the wrist 1, the space between the cuff band 12 and the wrist 1 can be reduced, shift of the cuff band 12 toward longitudinal direction and peripheral direction of the wrist 1 can be prevented, and therefore the blood pressure is stabilized, and the measurement accuracy of blood pressure can be further improved.

As described above, the present invention is explained based on the aforementioned embodiments, but the present invention is not limited thereto.

For instance, according to the present embodiment, in the cuff spring 13, the slit 28 is provided at a central position in the axial direction, and a portion excepting the mount portion 22 and the protrusion 26 of the cuff spring 13 is divided into the hand-side divided portion 29 and the arm-side divided portion 30. However, the slit 28 may be formed at a plurality of positions in the axial direction of the cuff spring 13, respectively to divide a portion excepting the mount portion 22 and the protrusion 26 of the cuff spring 13 into 3 or more, so that the curvatures of respective divided portions are subsequently increased from the hand side toward the arm side.

In addition, according to the above embodiment, in the cuff spring 13, the protrusion 26, the reinforcing rib 27 and the slit 28 are provided. However, the slit 28 may not be formed, although having the protrusion 26 and the reinforcing rib 27 provided, or the slit 28 may be formed, although not having the protrusion 26 and the reinforcing rib 27 provided.

Furthermore, according to the above embodiment, an example of attaching the cuff band 12 to the sphygmomanometer main body 11 is shown, but it is needless to say that like a general sphygmomanometer, the sphygmomanometer main body 11 and the cuff band 12 may be cut out from each other and separately formed.

What is claimed is:

1. A wrist sphygmomanometer formed in a curved shape to fit the semicircle on the side of the pulsation part of the wrist, comprising:
    a cuff spring having a mount portion outside;
    a cuff band including said cuff spring as a core, having an air bag disposed inside, and wound around the wrist; and
    a sphygmomanometer main body mounted on the mount portion of said cuff spring, comprising a pressure pump for supplying air to the air bag, wherein said cuff spring has a protrusion protruding inward formed at a nearly central position in the peripheral direction, said cuff spring has a slit formed at an arbitrary position in the axial direction so as to extend in a peripheral direction, and both sides of said slit in the axial direction of said cuff spring are formed having different curvatures with each other.

2. The wrist sphygmomanometer according to claim 1, wherein said cuff spring is provided with an reinforcing rib formed integrally with said protrusion to reinforce the protrusion.

3. A wrist sphygmomanometer comprising:
    a cuff spring formed in a curved shape to fit the semicircle on the side of the pulsation part of the wrist, and having a mount portion outside;
    a cuff band including the cuff spring as a core, having an air bag disposed inside, and wound around the wrist; and
    a sphygmomanometer main body mounted on the mount portion of said cuff spring, comprising a pressure pump for supplying air to the air bag,
    which is constructed so that in a cuff spring, a protrusion protruding inward is formed at an approximately a central position in a peripheral direction and,
    said cuff spring is provided with an reinforcing rib formed integrally with said protrusion to reinforce the protrusion.

* * * * *